United States Patent
Nennie et al.

(10) Patent No.: US 10,048,218 B2
(45) Date of Patent: Aug. 14, 2018

(54) SYSTEM AND A METHOD FOR NON-INVASIVE DATA ACQUISITION

(75) Inventors: Frans Antonius Nennie, Delft (NL); Andrea Neto, Delft (NL); Stefania Monni, Delft (NL)

(73) Assignee: NEDERLANDSE ORGANISATIE VOOR TOEGEPAST-NATUURWETEN SCHAPPELIJK ONDERZOEK TNO, Delft (NL)

( * ) Notice: Subject to any disclaimer, the term of this patent is extended or adjusted under 35 U.S.C. 154(b) by 863 days.

(21) Appl. No.: 13/978,881

(22) PCT Filed: Dec. 22, 2011

(86) PCT No.: PCT/NL2011/050889
§ 371 (c)(1),
(2), (4) Date: Oct. 15, 2013

(87) PCT Pub. No.: WO2012/096567
PCT Pub. Date: Jul. 19, 2012

(65) Prior Publication Data
US 2014/0028329 A1    Jan. 30, 2014

(30) Foreign Application Priority Data

Jan. 10, 2011   (EP) .................................. 11150508
Sep. 14, 2011   (EP) .................................. 11181278

(51) Int. Cl.
*A61B 5/00*       (2006.01)
*G01N 27/04*     (2006.01)
(Continued)

(52) U.S. Cl.
CPC .......... *G01N 27/04* (2013.01); *A61B 5/0507* (2013.01); *A61B 5/14557* (2013.01); *H01Q 1/273* (2013.01); *H01Q 13/10* (2013.01)

(58) Field of Classification Search
CPC .. A61B 5/0507; A61B 5/14557; G01N 27/04; H01Q 13/10; H01Q 1/273
See application file for complete search history.

(56) References Cited

U.S. PATENT DOCUMENTS 5,829,437 A * 11/1998 Bridges .................... A61B 5/05
324/638
7,586,464 B2    9/2009 Neto et al.
(Continued)

FOREIGN PATENT DOCUMENTS

EP    0694282    1/1996
EP    1803396    7/2007
(Continued)

OTHER PUBLICATIONS

International Search Report for PCT/NL2011/050889, dated Mar. 19, 2012 (3 pages).

*Primary Examiner* — Ruth S Smith
(74) *Attorney, Agent, or Firm* — Hoffmann & Baron, LLP (57) ABSTRACT

The invention relates to a system for non-invasive data acquisition from a human or animal body 7, comprising an antenna for irradiating a portion of the body, said antenna being connected to a source and a processor for collecting the data pursuant to the irradiation, wherein the antenna is a leaky wave antenna 1, 2, 3, 4 operable using a dielectric layer, the system being configurable so that the portion of the body 7 is at least partially used for the dielectric layer.

11 Claims, 9 Drawing Sheets

(51) Int. Cl.
  *A61B 5/05* (2006.01)
  *A61B 5/1455* (2006.01)
  *H01Q 1/27* (2006.01)
  *H01Q 13/10* (2006.01)

(56) References Cited

U.S. PATENT DOCUMENTS

2003/0036674 A1   2/2003   Bouton
2008/0319285 A1   12/2008  Hancock
2012/0088459 A1*  4/2012   Neto .................. H01Q 1/38
                                              455/73

FOREIGN PATENT DOCUMENTS

EP       2175522 A1    4/2010
WO     2006009432 A1   1/2006

* cited by examiner

SYSTEM AND A METHOD FOR NON-INVASIVE DATA ACQUISITION

FIELD OF THE INVENTION

The invention relates to a system for non-invasive data acquisition from a human or animal body, comprising an antenna for irradiating a portion of the said body, said antenna being connected to a source and a processor for collecting said data pursuant to said irradiation.

The invention further relates to a method for non-invasive data acquisition from a human or animal body.

BACKGROUND OF THE INVENTION

An embodiment of a system as is set forth in the opening paragraph is known from US2006/0025664. In the known system a rectangular waveguide is used to transmit a suitable RF signal to a body under investigation.

It is a disadvantage of the known system that a large size of a waveguide, a limited frequency band and an inferior impedance match cause substantially high reflections in the skin of the human or animal body which deteriorates accuracy of the collected data. In addition, the known system is not suitable for detecting small variations in the dielectric constant of the human or animal body (for example, due to local changes of a glucose level in blood flow).

A further embodiment of the system as is set forth in the opening paragraph is known from U.S. Pat. No. 6,463,336. In the known system an antenna used for irradiating a portion of a skin of a patient may be configurable to conform to an external shape of the body. Although this may at least partially solve a problem of impedance matching between the hardware used for irradiating and the body, the device known from U.S. Pat. No. 6,463,336 is not suitable for blood glucose concentration measurements due to a limited frequency bandwidth of the known system and a large aperture size.

SUMMARY OF THE INVENTION

It is an object of the invention to provide a system for non-invasive data acquisition from a human or animal body, wherein an improved impedance matching is realized. It is a further object of the invention to provide a system for non-invasive data acquisition from a human or animal body, wherein subtle variations of a local dielectric constant of the body are measurable accurately. It is a still further object of the invention to provide a system for non-invasive data acquisition from the human or animal body, which can be operable in the near-field and in the far-field. More in particular, it is a still further object of the invention to provide a system for non-invasive determination of a blood glucose level in the human or animal body.

To this end in the system according to the invention the antenna is a leaky wave antenna operable using a dielectric layer, the system being configured so that the portion of the body is used for at least partially forming the said dielectric layer.

It is found advantageous to use the portion of the body, such as skin, for the dielectric layer which is necessary for operation of the leaky wave antenna. The leaky wave antennas are known per se and their operation will not be described here in detail. Generally, the leaky wave antenna may comprise a waveguide provided with a slot.

Preferably, the system is configured so that the dielectric layer is formed by the portion of the body. It will be appreciated that in this case essentially no dielectric layer is provided on the system and the tissue is used to form a suitable dielectric layer necessary for operation of the system.

It is found that in the system according to the invention the impedance matching is improved considerably. It is further found that the system according to the invention is particularly suitable to be used for monitoring a subcutaneous part of a human or animal body due to:

i) low ringing;
ii) capability of high range and time resolution;
iii) a stable performance over a wide range of frequencies;
iv) superior impedance matching between the frontend, antenna and the skin;
v) substantial non-dispersivity with frequency;
vi) frequency independent phase centre;
vii) a substantial preservation of the amplitude of the transmitted pulse spectrum thereby avoiding pulse response distortion.

An embodiment of a system using a leaky wave antenna is known from EP 2175522. In the known system a substrate lens antenna is used, which is defined by a lens shaped dielectric body connected to a planar antenna structure. Accordingly, in the known device the lens shaped dielectric body focuses radiation emanating from a substantially planar structure. However, the known system is not readily applicable for non-invasive data acquisition from a surface of a human or animal body.

Because in the invention the dielectric layer necessary for operating of the leaky wave antenna is provided by the skin of a human or animal body, due to a high permittivity of the said body, a single beam can still be obtained for operation in the near field and in the far field.

In an embodiment of the system according to the invention the slot of the leaky wave antenna is provided on a substantially planar substrate layer. This has an advantage that the antenna may be manufactured in planar printed technology.

In a further embodiment of the system according to the invention the system comprises a plurality of leaky wave antennas.

It is found to particularly advantageous to provide the system with a plurality of antennas. In this way a suitable array of leaky wave antennas may be provided. In this configuration, some antennas may be operable to transmit RF energy into the skin, whereas other antennas may be operable to receive reflected radiation. However, it will be appreciated that the antennas may be suitably adapted to operate in both modes consecutively.

Preferably, the one or more leaky wave antennas are operable in the frequency range of 0.5-20 GHz. This has an advantage that a high range resolution may be obtained. This feature is particularly important for the far-field. In addition, this bandwidth allows carrying out spectral measurements in the microwave and millimeter wave region.

However, it will be appreciated that the frequency range set for the system according to the invention may be dependent on a particular application. Because the skin itself is a dielectric layer, the frequency range of the system according to the invention may be as broad as 0.5-75 GHz. However, when a fat layer is used for the dielectric layer of the system according to the invention the frequency range may be set to 6-75 GHz. More in particular, should the system according to the invention be connected to a 1.0 mm connector, the upper limit of the frequency range may be set to 110 GHz.

In a still further embodiment of the system according to the invention, the slot is tapering towards an exterior of the leaky wave antenna.

This feature is found to be advantageous for improving coupling of the antenna.

In a still further embodiment of the system the source supplying the leaky wave antenna is a radar or a N-port network.

It is found advantageous to use a FMCW or pulsed radar frontend to feed the leaky wave antenna of the system according to the invention. A FMCW/pulsed radar frontend can be coupled directly to the feed line of the leaky wave antenna. This has an advantage as connector losses and cable reflections losses may be avoided in this way. In addition an open wireless technology, such as WiFi, may be used for exchanging data to the processor. However, it will be appreciated that in the system according to the invention the processor may be built-in.

The method for non-invasive data acquisition from a human or animal body according to the invention comprises the steps of:

arranging a leaky wave antenna operable with a dielectric layer on a surface of the said body so that a portion of the surface forms at least a part of the dielectric layer;

irradiating the said portion using the leaky wave antenna.

In an embodiment of the method a plurality of leaky wave antennas is used to irradiate and/or to receive data from the body, wherein data collection is time gated with respect to irradiation.

In a further embodiment of the method according to the invention a two-dimensional array of leaky wave antennas is used for acquiring three-dimensional data from the said body.

These and other aspects of the invention will be discussed with reference to drawings wherein like reference signs correspond to like elements. It will be appreciated that the drawings are presented for illustrative purposes only and may not be used for limiting the scope of the appended claims.

DETAILED DESCRIPTION OF THE DRAWINGS

Figure 1:
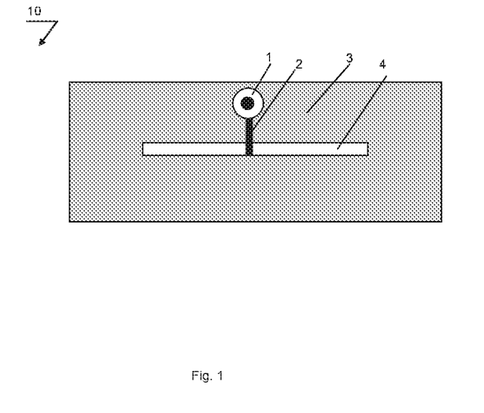
FIG. 1 presents in a schematic way an embodiment of a system according to the invention.

FIG. 1 presents in a schematic way an embodiment of a system according to the invention. The system 10 comprises an RF connector 1 provided on a micro strip feed line 2, which is connected to a dielectric substrate plate 3. The dielectric substrate plate 3 is provided with a slot 4 cut on an electrically conductive plate. It will be appreciated that a non-tapered slot may be used. This one-dimensional (1D) leaky-wave aperture distribution results in a "fanbeam" having a narrow shape in the xz plane (perpendicular to the plane of the figure), and a broad shape in the cross-plane. A "pencil beam" can be created by using an array of such 1D radiators. Unlike the slow-wave structure, a very narrow beam can be created using the antenna as is shown in FIG. 1. Since leakage occurs over the length of the slot in the wave guiding structure, the whole length constitutes the antenna's effective aperture. A large attenuation constant $\alpha$ implies a short effective aperture, so that the radiated beam has a large beam width. Conversely, a low value of a results in a long effective aperture and a narrow beam, provided the physical aperture is sufficiently long.

The leaky wave antenna as is depicted in FIG. 1 may be connected to a radar or a N port network for feeding energy and a processor for collecting acquired data. In accordance with the invention the leaky wave antenna is to be directly applied to the skin so that the skin forms a dielectric layer for coupling radiation emanating from the antenna towards inner layers of the patient. The radiation emanating from the leaky wave antenna may be used for locating a relevant hypodermic vessel, for example by measuring dielectric losses. When such vessel is detected reflections are measured for determining the vessel RF conductivity which is a suitable measure of the blood glucose content. The radiation may also be used for locating an anomaly (e.g. tumor) through reflection caused by the dielectric interface. Accordingly data acquired from the human or animal body using the arrangement according to the invention may relate to a glucose level in a blood stream or to a dielectric contrast of a tumor in the said body.

Figure 2:
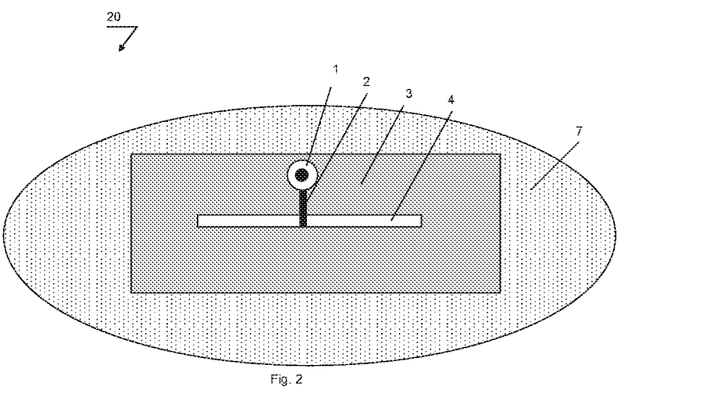
FIG. 2 presents in a schematic way a top view of the embodiment depicted in FIG. 1.

FIG. 2 presents in a schematic way a top view of the embodiment depicted in FIG. 1 when applied to a portion of the skin 7. It will be appreciated that in accordance with the invention the body's skin forms a substantial portion of the dielectric layer necessary for operating of the leaky wave antenna. Accordingly, the structure as is depicted in FIG. 1 may be provided with a relatively thin dielectric layer covering the slot 4 and the substrate 3. More in particular, the antenna as is shown in FIG. 1 may be provided with a separation dielectric layer, on top of the substrate 3 forming the slot 4.

Figure 3:
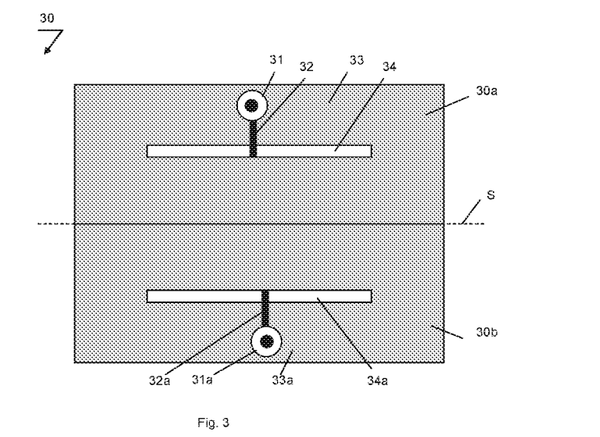
FIG. 3 presents in a schematic way an embodiment of the system depicted in FIG. 1 consisting of two leaky wave antenna structures.

FIG. 3 presents in a schematic way a bottom view of an embodiment of the system depicted in FIG. 1 consisting of two leaky wave antenna structures. In this particular embodiment of the system 30, two leaky wave antennas 30a, 30b are used, which are symmetrically arranged with respect to a symmetry line S. The leaky wave antennas comprise respective RF connectors 31, 31a, respective feed lines 32, 32a, respective dielectric substrates 33, 33a and respective slots 34, 34a. It will be appreciated that in an alternative embodiment some of the structures may be shared. For example, the two antennas may share the same substrate layer. It will be further appreciated that the RF connectors 31, 31a may be soldered on the respective micro strip feed lines.

It is found that with the configuration 30 it is possible to perform S21 transmission measurements on the skin. This can lead to a substantial improvement of the accuracy of measurement of the dielectric constant. For purposes of S21 transmission measurement one connector may be used as the transmission connector and can function as a reference. The other connector may be used as the receiving connector for receiving the non-invasive measurement data.

It will be further appreciated that a suitable array of leaky wave antennas may comprise more than two individual leaky wave antenna structures. It is found that a combination of two or more antenna structures can be used to measure a change in skin humidity, for example.

It is further found that a two-dimensional array of the leaky wave antenna structures as is discussed with reference to FIG. 1 may be provided for carrying out a three-dimensional measurement. For example, the two-dimensional array may be connected to a radar system and can be positioned on the skin. The corresponding transmission losses in the body layers may be used for selecting an appropriate frequency band of the antenna. Generally, it is found that the system according to the invention has superior operational characteristics in the frequency range of 0.5-20 GHz.

Figure 4:
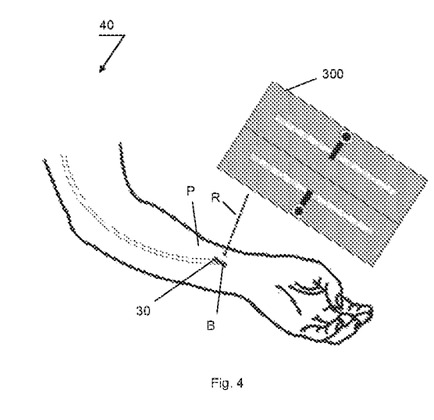
FIG. 4 presents in a schematic way an embodiment of the system according to the invention comprising a double antenna configuration.

FIG. 4 presents in a schematic way an embodiment of the system according to the invention comprising a double antenna configuration. For example, the structure 30, discussed with reference to FIG. 3, may be positioned on an extremity of a patient P, such as an arm. It will be appreciated that item 300 represents an exaggerated view of the system 30 schematically shown on the patient P. Radiation R, depicted schematically, is emanating from the system 30 and may be used for locating a suitable blood vessel B. The system 30 is found to be very suitable for detecting the glucose level in a blood flow of the patient P.

Figure 5:
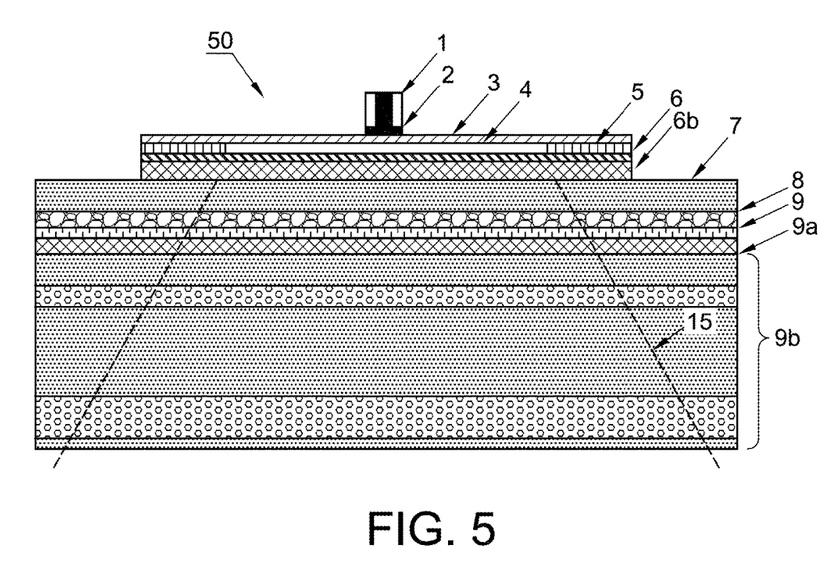
FIG. 5 presents in a schematic way lateral view of the system depicted in FIG. 1.

FIG. 5 presents in a schematic way lateral view of the system depicted in FIG. 1. It is found that when the antenna structure discussed with reference to FIG. 1 is positioned on a patient's skin minimal RF reflection occur due to the fact that the skin acts as a dielectric layer of the leaky wave antenna thereby suitably coupling radiation emanating from the antenna to the body. The outer skin surface is schematically depicted by a layer 7. Layers 8, 9 and 9b schematically represent further skin layers. The layer 7 may represent the stratum corneum, the layer 8 may represent stratum lucidum and so forth. Respective skin layers may cause individual reflections, which are discussed with reference to FIGS. 7 and 8.

It will be appreciated that in this particular embodiment the layer 6b represents an intermediate (partial) dielectric antenna layer. The radiation beam 15 propagating inside the skin layers is emanating from the slot 4. The layer 5 represents the copper layer and the layer 6 may correspond to a foam layer which may be advantageous for enabling surface flexibility of the leaky wave antenna.

Figure 6:
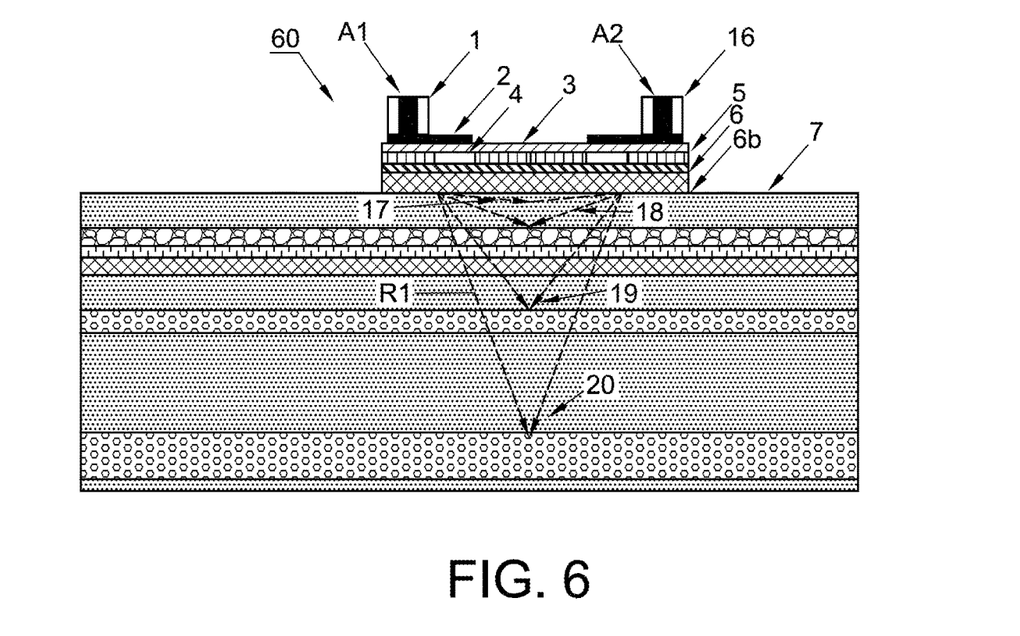
FIG. 6 presents in a schematic way lateral view of the system depicted in FIG. 4.

FIG. 6 presents in a schematic way lateral view of the system depicted in FIG. 4. In this particular embodiment an antenna array comprising two symmetrically arranged individual antennas A1, A2 is presented. The structure of the antenna array is similar to the structure of the system as is discussed with reference to FIG. 3. Accordingly, the array is positioned on the skin so that the slots are facing the skin surface. A resulting radiation beam R1 is a convolution of the individual radiation beams emanating from the individual slots of the respective antennas.

It is found that such configuration is useful for carrying out the S21 transmission measurement. The S21 transmission measurement using two antennas is capable of measuring the transmission of the direct and indirect (reflected) signals. The first signal 17 is the direct transmission signal through the intermediate layer 6b and the transmission between the intermediate layer 6b and the stratum corneum 7.

It is found that this signal can be very strong. The second signal 18 originates indirectly from reflections of the stratum lucidum 8 layer combined with the direct transmission signal through the stratum corneum. This signal is found to be proportional to the humidity of the stratum corneum and can be used as an embodiment of a suitable non-invasive data.

The reflections 19 of the papillary layer containing small blood vessels can be poorly distinguishable from the reflections of the other epidermis layers. The reflections 20 of the artery and vein in the hypodermis can be easily distinguished because the corresponding skin layer is relatively thick.

It is found to be possible to use time gating by means of the wide frequency band of the leaky wave antenna in the system according to the invention. The principles of time gating are discussed with reference to FIGS. 7 and 8.

Figure 7:
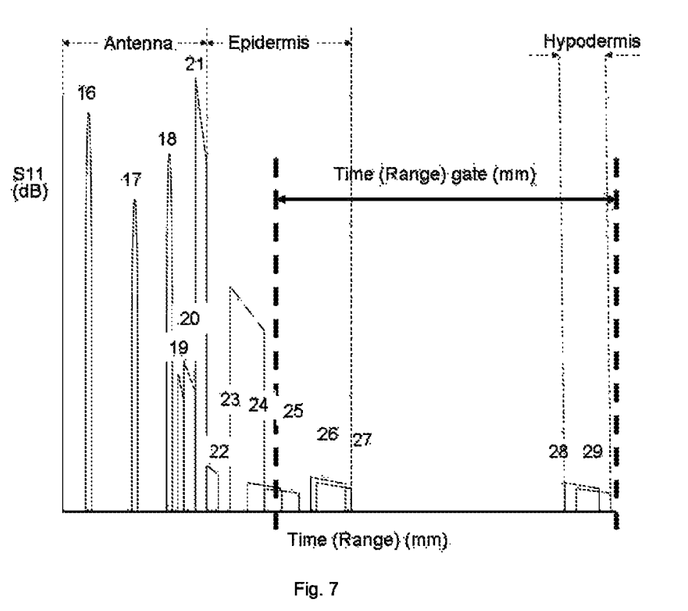
FIG. 7 presents schematically an exemplary embodiment of the S11 parameter response (Reflection) obtainable from the system according to the invention.

FIG. 7 presents schematically an exemplary embodiment of the S11 parameter response (Reflection) obtainable from the system according to the invention. Reflections, caused by the skin layers are schematically depicted as respective dotted lines. It is found that s suitable time gating may be used for eliminating undesirable reflections in the antenna and the underlying skin. FIG. 7 presents a time domain plot.

The time domain data can be calculated by performing a Fast Fourier Transform (FFT) over the measured data in the frequency domain. Those skilled in the art would readily appreciate the corresponding calculation method, which is per se known.

The S11 and S21 are presented as a function of time. The amplitude and the range width of the response peaks S11 and S21 signals are depicted schematically, not on scale.

The S11 reflections in the antenna are given by the response peaks 16-21 in FIG. 7. These reflections correspond to the impedance transmissions of the antenna parts 1-6 (see FIGS. 1 and 6) and of the skin layer, the latter being given by peaks 22-29.

The response peak 21 of the dielectric layer 6b (shown in FIG. 6) is expected to be relatively large in comparison with the reflection from the blood vessels, see peak 25, for example.

It is found that by placing a time gate corresponding to the time of arrival of peak 25 enables isolation of this peak from the undesirable and non-informative responses. The wide range of the leaky wave antenna as is discussed in the foregoing enables time gating with a considerably narrow gate width.

It is found that the system according to the invention allows for pulse response amplitude and phase preservation and, therefore, accurate time gating can be enabled. In addition, precise determination of the position of the interfaces in the skin which cause reflections is enabled as well.

By means of example, if the gate is placed over the artery and veins, see pulses 28, 29 small changes in the peak responses may be measured. After an Inverse FFT the small changes in phase can be measured in the frequency domain and small changes in dielectric constant of the blood. Such changes may be representative of the blood glucose level and of the presence of anomalies in the human or animal body, such as a tumor.

Figure 8:
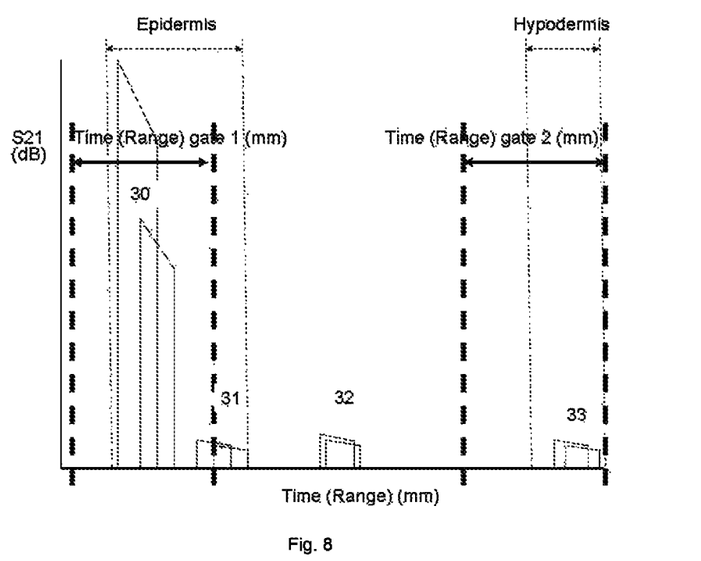
FIG. 8 presents schematically an exemplary embodiment of the S21 parameter response (Transmission) obtainable from the system according to the invention.

In order to achieve a better accuracy, the results of time gated S21 peak responses can be combined with the S11 responses, which are representative of transmission, see peak 29 of FIG. 7 and peak 33 of FIG. 8.

FIG. 8 presents schematically an exemplary embodiment of the S21 parameter response (Transmission) obtainable from the system according to the invention. It will be appreciated that the peaks 30, 31 correspond to the epidermis transmission, while the peak 33 correspond to the hypodermis transmission. By selecting the peak response 30, corresponding to item 17 of FIG. 6, for example, by time gating, skin humidity determination may be enabled.

Figure 9:
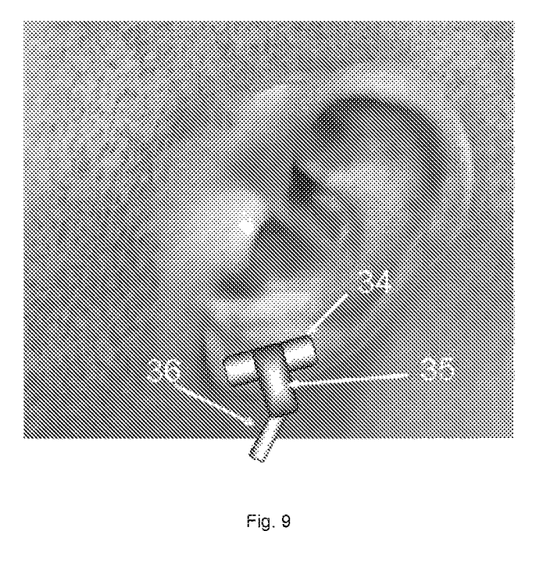
FIG. 9 presents in a schematic way an embodiment of the system provided with two leaky wave antennas and being applied to an ear of a person.

FIG. 9 presents in a schematic way an embodiment of the system provided with two leaky wave antennas and being applied to an ear of a person. In this particular example two or more leaky wave antenna structures are placed on both sides of an ear lobe. On this location an antenna clamp 35 connected to the leaky wave antenna structures 34 may provide a stable connection to the ear lobe. A cable 36 connecting to the antennas can be plugged into a computer for data communication and power supply.

While specific embodiments have been described above, it will be appreciated that the invention may be practiced otherwise than as described. Moreover, specific items discussed with reference to any of the isolated drawings may freely be inter-changed supplementing each outer in any particular way. The descriptions above are intended to be illustrative, not limiting. Thus, it will be apparent to one skilled in the art that modifications may be made to the invention as described in the foregoing without departing from the scope of the claims set out below.

The invention claimed is:

1. A method for non-invasive data acquisition associated with at least one portion of a human or animal body portion, comprising:
   irradiating at least one portion of the body, using at least one leaky wave antenna comprising a waveguide associated with a surface of the at least one portion of the body, the waveguide comprising a slot in an electrically conductive plate, the irradiation being generated as a leaky wave;
   generating, using a source, a guided wave traveling along the slot, the at least one portion of the body coupling the guided wave to the leaky wave, whereby leakage from the guided wave occurs over a length of the slot, the at least one portion of the body being irradiated at a pre-determined frequency range such that reflected signals include measurement data associated with the at least one portion of the body with minimal undesirable reflection signals;
   receiving the reflected signals including the measurement data;
   transmitting the measurement data to a processor;
   processing the measurement data associated with the irradiation of the at least one portion of the body, the measurement data being used in identifying an anomaly related with the at least one portion of the body; and
   enabling a determination of informative data associated with the at least one portion of the body with minimized undesirable signal reflections, by suitably coupling radiation emitted from the at least one leaky wave antenna to the at least one portion of the body.

2. The method according to claim 1, further comprising the at least one leaky wave antenna irradiating the at least one portion of the body, wherein an intermediate dielectric is used that is intermediate the at least one portion of the body and the slot, the intermediate dielectric increasing surface flexibility.

3. The method according to claim 1, wherein the slot is provided on a substantially planar substrate layer with a length of the slot related to an effective aperture of the at least one leaky wave antenna, the effective aperture being inversely proportional to an attenuation constant of a beam emanating from the at least one leaky wave antenna.

4. The method according to claim 1, further comprising irradiating the at least one portion of the body, using an array of leaky wave antennas associated with the at least one portion of the body.

5. The method according to claim 1, further comprising irradiating the at least one portion of the body, using the at least one leaky wave antenna that operates in transmit and/or receive mode.

6. The method according to claim 1, wherein the source is operable in the frequency range of 0.5-20 GHz.

7. The method according to claim 1, further comprising irradiating the at least one portion of the body, using a two-dimensional array of leaky wave antennas.

8. The method according to claim 1, further comprising irradiating the at least one portion of the body, using at least two leaky wave antennas that are symmetrically arranged.

9. The method according to claim 1, wherein the source is coupled directly to a feed line of the at least one leaky wave antenna, the source including one of a frequency-modulated continuous-wave (FMCW) radar, a pulsed radar and an N-port network.

10. The method according to claim 1, further comprising enabling the determining of informative data that relates to a glucose level or a dielectric contrast of a tumor associated with the at least one portion of the body.

11. The method according to claim 1, further comprising determination of the informative data based on a time gating of received data within a time interval.

\* \* \* \* \*